(12) United States Patent
Gobl (10) Patent No.: US 10,058,230 B2
(45) Date of Patent: Aug. 28, 2018

(54) CARRIER ARRANGEMENT FOR STORING AND/OR TRANSPORTING AND/OR CLEANING DISHWARE OR OTHER ITEMS

(71) Applicant: FRIES Planungs—und Marketinggesellschaft m.b.H., Sulz (AT)

(72) Inventor: Otmar Gobl, Altach (AT)

(73) Assignee: FRIES Planungs- und Marketinggesellschaft m.b.H., Sulz (AT)

(*) Notice: Subject to any disclaimer, the term of this patent is extended or adjusted under 35 U.S.C. 154(b) by 20 days.

(21) Appl. No.: 15/209,872

(22) Filed: Jul. 14, 2016

(65) Prior Publication Data

US 2017/0027411 A1 Feb. 2, 2017

(30) Foreign Application Priority Data

Jul. 30, 2015 (AT) .................................. GM225/2015
Mar. 22, 2016 (EP) ..................................... 16161697

(51) Int. Cl.
*A47L 15/50* (2006.01)
*B08B 13/00* (2006.01)
(Continued)

(52) U.S. Cl.
CPC .............. *A47L 15/50* (2013.01); *A47B 55/00* (2013.01); *A47B 81/00* (2013.01); *A47L 15/505* (2013.01);
(Continued)

(58) Field of Classification Search
CPC .............. B65D 19/385; B65D 19/0002; B65D 2519/00024; B65D 2519/00034;
(Continued)

(56) References Cited

U.S. PATENT DOCUMENTS 3,830,134 A * 8/1974 Erickson ............... F16B 37/043
411/15
3,869,958 A * 3/1975 Murayama ............ F16B 21/076
411/15

(Continued)

FOREIGN PATENT DOCUMENTS

DE 7110537 6/1971
DE 3523810 1/1987

(Continued)

OTHER PUBLICATIONS

Tech tray™ Organizer, Intelligent workpiece carrier system Safe—Clean—Flexible, www.fries.at, 4 pages (Jan. 1, 2015) (admited prior art).

(Continued)

*Primary Examiner* — Hiwot E Tefera
(74) *Attorney, Agent, or Firm* — Volpe and Koeing, P.C.

(57) ABSTRACT

Carrier arrangement (1) for storing and/or transporting and/or cleaning dishware or other items, wherein the carrier arrangement (1) has at least one carrier plate (2) with at least one lattice-shaped structure (3), wherein the lattice-shaped structure (3) is formed by lattice rods (5) which are arranged in a rectangular shape, in particular a square shape, and surround rectangular, in particular square, openings (4), and wherein the carrier arrangement (1) has at least one fastening base (6) which is fastenable or fastened with a clamping action on the lattice-shaped structure (3), wherein the fastening base (6) is fastenable or fastened with a clamping action in one of the rectangular, in particular square, openings (4).

16 Claims, 8 Drawing Sheets

(51) Int. Cl.
  *B65D 19/00* (2006.01)
  *B65D 19/44* (2006.01)
  *A47B 55/00* (2006.01)
  *A47B 81/00* (2006.01)
  *A61L 2/26* (2006.01)
  *A61L 2/00* (2006.01)
  *A61B 50/20* (2016.01)
  *A61B 50/33* (2016.01)
  *A61B 50/34* (2016.01)
  *A61B 50/30* (2016.01)

(52) U.S. Cl.
  CPC .............. *A61L 2/26* (2013.01); *B08B 13/00* (2013.01); *B65D 19/0002* (2013.01); *B65D 19/44* (2013.01); *A61B 50/20* (2016.02); *A61B 50/33* (2016.02); *A61B 50/34* (2016.02); *A61B 2050/3011* (2016.02); *A61L 2/00* (2013.01); *B65D 2519/00034* (2013.01); *B65D 2519/00069* (2013.01); *B65D 2519/00268* (2013.01); *B65D 2519/00288* (2013.01); *B65D 2519/00308* (2013.01); *B65D 2519/00318* (2013.01); *B65D 2519/00348* (2013.01); *B65D 2519/00363* (2013.01); *B65D 2519/00815* (2013.01)

(58) Field of Classification Search
  CPC .......... B65D 2519/00059; B65D 2519/00069; B65D 2519/00268; B65D 2519/00288; B65D 2519/00308; B65D 2519/00318; B65D 2519/00348; B65D 2519/00363; B65D 2519/00676; B65D 2519/00815; B65D 2519/0097; B65D 85/00; B65D 1/34; B25H 3/00; B25H 3/003; A61B 50/33; A61B 50/34; A61B 50/22; A61B 50/20; A61B 50/30; A61B 2050/0074; A47L 15/50; A47L 15/505; A47B 81/00; A47B 55/00; B08B 13/00; A61L 2/00; A61L 2/26
  USPC .... 108/55.3, 56.3, 901, 56.1, 51.3; 206/349, 206/373, 377, 378, 553; 248/73, 74.1; 211/41.1–41.7, 70.6, 69, 126.1, 85.13
  See application file for complete search history.

(56) References Cited

U.S. PATENT DOCUMENTS

| | | | | |
|---|---|---|---|---|
| 4,077,300 A | | 3/1978 | Yoda | |
| 4,704,059 A * | | 11/1987 | Nakama | F16B 37/043 411/182 |
| 4,927,306 A * | | 5/1990 | Sato | F16B 33/004 411/182 |
| 5,666,886 A * | | 9/1997 | Alexander | B65D 19/0069 108/56.3 |
| 5,794,543 A * | | 8/1998 | John | B65D 19/0022 108/56.1 |
| 5,827,487 A * | | 10/1998 | Holmes | A61L 2/26 206/370 |
| 5,855,274 A * | | 1/1999 | Piao | B25H 3/02 206/373 |
| 6,048,503 A * | | 4/2000 | Riley | A61L 2/26 206/370 |
| 6,244,447 B1 * | | 6/2001 | Frieze | A61L 2/07 206/370 |
| 6,436,357 B1 * | | 8/2002 | Frieze | A61L 2/26 206/263 |
| 7,601,312 B2 * | | 10/2009 | Riley | A61L 2/26 248/309.1 |
| 7,722,837 B2 * | | 5/2010 | Riley | A61L 2/26 206/363 |
| 7,861,860 B2 * | | 1/2011 | Bettenhausen | A61L 2/18 206/370 |
| 8,069,998 B2 * | | 12/2011 | Thomas | A61L 2/26 211/85.13 |
| 8,371,444 B1 * | | 2/2013 | Huang | B25H 3/003 206/373 |
| 8,505,720 B2 * | | 8/2013 | Huang | B25H 3/00 206/349 |
| 2008/0116095 A1 * | | 5/2008 | Riley | A61L 2/26 206/363 |
| 2013/0118938 A1 * | | 5/2013 | Huang | B25H 3/00 206/372 |

FOREIGN PATENT DOCUMENTS

| | | |
|---|---|---|
| DE | 202012103711 | 1/2013 |
| DE | 202014102215 | 7/2014 |
| EM | 003039189-01 | 3/2016 |
| EM | 003039189-02 | 3/2016 |
| EM | 003039189-03 | 3/2016 |
| EM | 003039189-04 | 3/2016 |
| EP | 2860126 | 4/2015 |
| EP | 2860127 | 4/2015 |
| EP | 2886482 | 6/2015 |

OTHER PUBLICATIONS

Tech rack, Industrial Baskets 600×400, 16 pages (Jan. 1, 2015) (admitted prior art).

\* cited by examiner

CARRIER ARRANGEMENT FOR STORING AND/OR TRANSPORTING AND/OR CLEANING DISHWARE OR OTHER ITEMS

INCORPORATION BY REFERENCE

The following documents are incorporated herein by reference as if fully set forth: Austrian Patent Application No. GM225/2015, filed Jul. 30, 2015; and European Patent Application No. 16 161 697.4, filed Mar. 22, 2016.

BACKGROUND

The present invention relates to a carrier arrangement for storing and/or transporting and/or cleaning dishware or other items, wherein the carrier arrangement has at least one carrier plate with at least one lattice-shaped structure, wherein the lattice-shaped structure is formed by lattice rods which are arranged in a rectangular shape, in particular a square shape, and surround rectangular, in particular square, openings, and wherein the carrier arrangement has at least one fastening base which is fastenable or fastened with a clamping action on the lattice-shaped structure.

In commercial dishwashing and also in the industrial cleaning of parts and in the sterilization of medical appliances and the like, carrier arrangements of the type in question are needed such that the parts to be cleaned or sterilized or the dishware are suitably stored during the cleaning or sterilizing process.

In addition, carrier arrangements of the type in question can also be used otherwise in logistics, in particular industrial logistics for transport and/or storage of structural parts, dishware and the like. A carrier arrangement of the type in question is known from FIGS. 12 and 15 of DE 20 2014 102 215 U1. The fastening base of the holding pins shown there is fastened with a clamping action on the lattice rods in the intersection area of two such lattice rods. This has the effect that a total of four openings are needed in order to fasten a fastening base with a clamping action on the lattice-shaped structure. Practical experience shows that this type of fastening of the fastening base on the lattice-shaped structure is relatively unstable, such that it can happen in practice that the fastening base is inadvertently released from the lattice-shaped structure.

DE 20 2014 102 215 U1 discloses, in FIG. 13, fastening bases of a second type in the form of a bayonet catch. However, to be able to fasten these in a carrier plate, the carrier plate requires openings specially adapted to this shape, as are shown in FIG. 14 of DE 20 2014 102 215 U1. These openings are no longer rectangular and are therefore not of the type in question here. They have the disadvantage that such openings take up a relatively large space, with the result that the openings have to be spaced apart relatively far from one another, as a result of which the flexibility as regards the positioning of the fastening base in the lattice-shaped structure is limited. Moreover, such lattice-shaped structures having non-rectangular openings, and therefore not of the type in question here, are often relatively susceptible to accumulation of dirt and the like.

SUMMARY

In a carrier arrangement of the abovementioned type with a lattice-shaped structure having rectangular openings, in particular square openings, the object of the invention is to propose a means by which the fastening base can be fastened in the lattice-shaped structure in a way that takes up a minimal amount of space and yet affords stability.

To this end, the invention proposes that the fastening base is fastenable or fastened with a clamping action in one of the rectangular, in particular square, openings.

Thus, in contrast to the abovementioned prior art, an underlying concept of the invention is to fasten a fastening base with a clamping action in an individual rectangular, in particular square, opening of the lattice-shaped structure. In other words, just one of the rectangular, in particular square, openings is needed in order to fasten the fastening base with a clamping action. If necessary, it is thereby possible, for example, for respective fastening bases to be fastened with a clamping action in directly adjacent rectangular, in particular square, openings. In this way, the fastening bases can be arranged very close to each other, if this is desirable for the specific case of use. This provides maximum freedom as regards the choice of the opening and therefore the position, on the carrier plate, in which the respective fastening base is to be fastened with a clamping action. There is therefore great flexibility in the way the carrier arrangement is equipped. Moreover, it has been surprisingly shown that very stable fastening can be achieved if a fastening base is fastened with a clamping action in just one of the rectangular, in particular square, openings.

To avoid incorrect interpretations, it will be noted, for the sake of completeness, that the invention does not mean that a fastening base can be fastened with a clamping action only in a single one of the rectangular, in particular square, openings and not in any other opening. Instead, provision is particularly made in the invention that, by virtue of the preferably identical configuration of the rectangular, in particular square, openings, a single fastening base can be fastened in a plurality of different ones of these openings. However, provision is likewise made according to the invention that a single one of these openings suffices for fastening the fastening base with a clamping action therein and therefore on the carrier plate.

As has already been mentioned above, carrier arrangements according to the invention are suitable and/or provided for storing and/or transporting and/or cleaning dishware or other items. In particular, they can be used in commercial dishwashing and/or in the industrial cleaning of parts. Carrier arrangements according to the invention can also be put to particularly good use in the sterilization of medical appliances, for example. The storage, in particular industrial storage, and the transport, in particular industrial transport, of dishware and other items are also among the sectors in which carrier arrangements according to the invention can be used or for which they can be provided.

The invention provides a very flexible modular system with which the carrier arrangement can be adapted to the respective purpose, i.e. in particular to the items to be stored in and/or on it, e.g. the dishware or the industrial components or the appliances to be sterilized. Thus, on the one hand, the fastening bases can be fastened at the desired positions on the carrier plate. On the other hand, a wide variety of supporting structures or other structures can be fastened on the fastening bases. In this connection, said supporting structures or other structures can be fixed or fastened on the fastening base either integrally or via a connecting means, preferably a connecting means that can be released without destruction, e.g. a thread or the like. Particularly preferably, provision is made that the fastening base has a connecting means releasable without destruction, preferably in the form of a threaded bush, in order to fasten a supporting structure or another structure on the fastening base. The threaded bush can be made of metal, for example. The supporting structures or other structures can be, for example, pins, webs, walls, grips, cross-shaped, fir-tree-shaped, multi-fingered or rod-shaped uprights, or also uprights that serve to allow several carrier arrangements to be stacked on top of each other. In principle, a wide variety of different structures can be fastened on the fastening bases, such that the carrier arrangement can, if necessary, be adapted to the specific use. With a corresponding wall-shaped structure, an embodiment of the carrier arrangement as a basket is possible in particular.

The carrier plate can have the lattice-shaped structure and also other areas that are not lattice-shaped. However, the carrier plate can also be designed completely as a lattice-shaped structure. The rectangular, in particular square, openings can be through-openings extending all the way through the carrier plate, but they can also be blind holes or the like. The lattice rods can have very different designs. For example, they can be rib-shaped and/or web-shaped structures or the like. However, in preferred embodiments of the invention, provision is made that the lattice rods surrounding the openings each have at least one bead for fastening the fastening base with a clamping action in the opening. The bead is an area that has a wider cross section compared to the rest of the lattice rod. The bead may have a circular cross section at least in parts, although this does not have to be the case. It can also have other shapes, for example the structure of a mushroom head or the like. For example, one or more undercuts can also be integrally formed on the bead, which undercuts help to fasten the fastening base with a clamping action in the opening. The bead is at any rate expediently configured on a face of the lattice rods that forms a surface of the carrier plate. Particularly preferably, provision is made that all of the beads of the carrier plate terminate in a common plane and/or form a common plane. In other words, in preferred embodiments, all of the beads extend by the same distance above the other areas of the lattice rods, such that their ends pointing away from the other areas of the lattice rods all lie in a common plane.

In preferred embodiments, ribs and/or web-shaped structures of the lattice rods are integrally formed on the bead, preferably on all of the beads. This preferably entails the ribs and/or web-shaped structures being integrally formed in one piece on the beads. The ribs and/or web-shaped structures of the lattice rods all expediently protrude from the beads on the same side of the carrier plate. With such ribs and/or web-shaped structures, it is possible to substantially improve the stability or load-bearing capacity of the carrier plate.

The edge length of the rectangular, in particular square, openings of the lattice-shaped structure expediently lies in the range of 4 mm (millimeters) to 35 mm, particularly preferably in the range of 6 mm to 18 mm.

In preferred embodiments of the invention, provision is made that the fastening base has at least two, preferably four, latching tongues lying opposite each other in pairs.

Particularly preferably, provision is made that each of the latching tongues for fastening the fastening base in the opening engages behind the bead of one of the lattice rods surrounding the opening. Like the bead, the latching tongues can also be provided with undercuts, which support or improve the stability of the clamped fastening of the fastening base in the respective opening. Provision is preferably made that the latching tongues have undercuts for engaging behind a bead. Moreover, provision can be made that, in order to facilitate an elastic deformation of the latching tongues, a gap is arranged preferably in each case between two respectively adjacent latching tongues.

Provision can also be made that the fastening base has a plate, wherein the bead is clampable or clamped, preferably in a manner free of play, between undercuts of the latching tongues and of the plate, wherein the undercuts of all the latching tongues of the fastening base are at the same distance from the plate.

Provision is also preferably made that the latching tongues lying opposite each other in pairs are elastically pre-stressed, preferably in a direction away from each other. Elastic prestressing is to be understood here as meaning in particular that the latching tongues, when moved from a starting position, are subject to elastic restoring forces that are so directed that they prestress the latching tongues in the direction of the starting position of the latter. The latching tongues do not have to be elastically pre-stressed in the starting position itself.

For optimal adaptation to the rectangular or in particular square shape of the openings, preferred variants of the invention are ones in which the fastening base has four latching tongues, and these latching tongues extend at least in part along the sides of an imaginary rectangle, in particular a square. In order to fasten the fastening base with a clamping action in the opening and/or to release it again from this clamped fastening, preferred variants are ones in which the fastening base, preferably in the area between the latching tongues, has at least one recess for the engagement of a rotary tool. The shape of the recess can be adapted here to specific rotary tools, e.g. screwdrivers, Allen keys and the like. They can therefore be slit-shaped or cross-shaped recesses or recesses for Allen keys, for example.

However, another type of recess can serve to receive an expansion pin or an expansion screw. This recess for receiving an expansion pin or an expansion screw is particularly preferably formed between the latching tongues of the fastening base. It can serve the purpose that an expansion pin inserted into the recess or an expansion screw screwed into it prevents the latching tongues from being able to be deflected. In this way, the fastening base can be fastened with a particularly firm and stable clamping action in the opening. Provision can thus be made that an expansion pin or an expansion screw is received in a recess of the fastening base between latching tongues of the fastening base.

There are different variants as regards the way in which the fastening base is introduced into the opening and thus as regards the types of embodiment of the fastening base. In a first group of these variants, provision is made that the fastening base is fastenable or fastened with a clamping action on the lattice-shaped structure exclusively by means of the fastening base, preferably its latching tongues, being pressed, preferably linearly, into the opening. In other words, in these variants, the fastening base is simply pressed a sufficient distance into the opening. In preferred variants, there is then an elastic deflection of the latching tongues on the beads of the lattice rods. In the end position, in which the fastening base is fastened with a clamping action in the opening, the latching tongues then expediently engage behind the bead.

By contrast, in another group of fastening bases according to the invention, provision can however also be made that the fastening base is fastenable or fastened with a clamping action on the lattice-shaped structure preferably exclusively by means of the fastening base, preferably its latching tongues, being inserted, preferably linearly, into the opening and by means of the fastening base then being rotated in the opening. This type of fastening base thus forms a kind of bayonet catch which however, in contrast to the aforementioned prior art, can be fastened in rectangular, in particular square, openings. This type of fastening base is particularly insusceptible to wear and can thus be used more permanently. Particularly in these variants, provision is expediently made that intermediate faces are provided between the latching tongues of the fastening base, which intermediate faces are less distant than the latching tongues themselves from the rotation axis about which the fastening base is rotated in the opening. Provision can thus be made that an intermediate face of the fastening base is located between two respectively adjacent latching tongues, wherein the intermediate faces are arranged at a shorter distance than the latching tongues from a rotation axis of the fastening base. Seen in a plan view, the latching tongues and the intermediate faces can provide an octagonal structure. This structure expediently has axial symmetry and/or point symmetry. These intermediate faces can, for example, be oriented parallel to the lattice rods upon insertion of the fastening base into the opening. By rotation of the fastening base in the opening, the latching tongues of the fastening base then come to engage on the lattice rods or particularly preferably on the beads thereof, resulting in the fastening base being fastened with a clamping action in the opening on the lattice-shaped structure. To release such fastening bases from the clamped fastening, the fastening bases can either be rotated onward, or they can be rotated back counter to the direction of insertion. Thereafter, the fastening bases can be removed again from the openings. The intermediate faces expediently lie parallel again to the lattice rods.

In carrier arrangements according to the invention, the carrier plate and also the fastening bases can in principle also be produced from metal, ceramic or other materials. In particularly preferred embodiments of the invention, provision is made that the carrier plate and/or the fastening base are/is made at least partially, preferably completely, from plastic. Such carrier plates and/or fastening bases can expediently be produced, for example, from thermoplastic, particularly preferably as injection-molded parts.

BRIEF DESCRIPTION OF THE DRAWINGS

Further features and details of preferred embodiment variants of the invention are explained below with reference to the figures, in which.

DETAILED DESCRIPTION OF THE PREFERRED EMBODIMENTS

Figure 1:
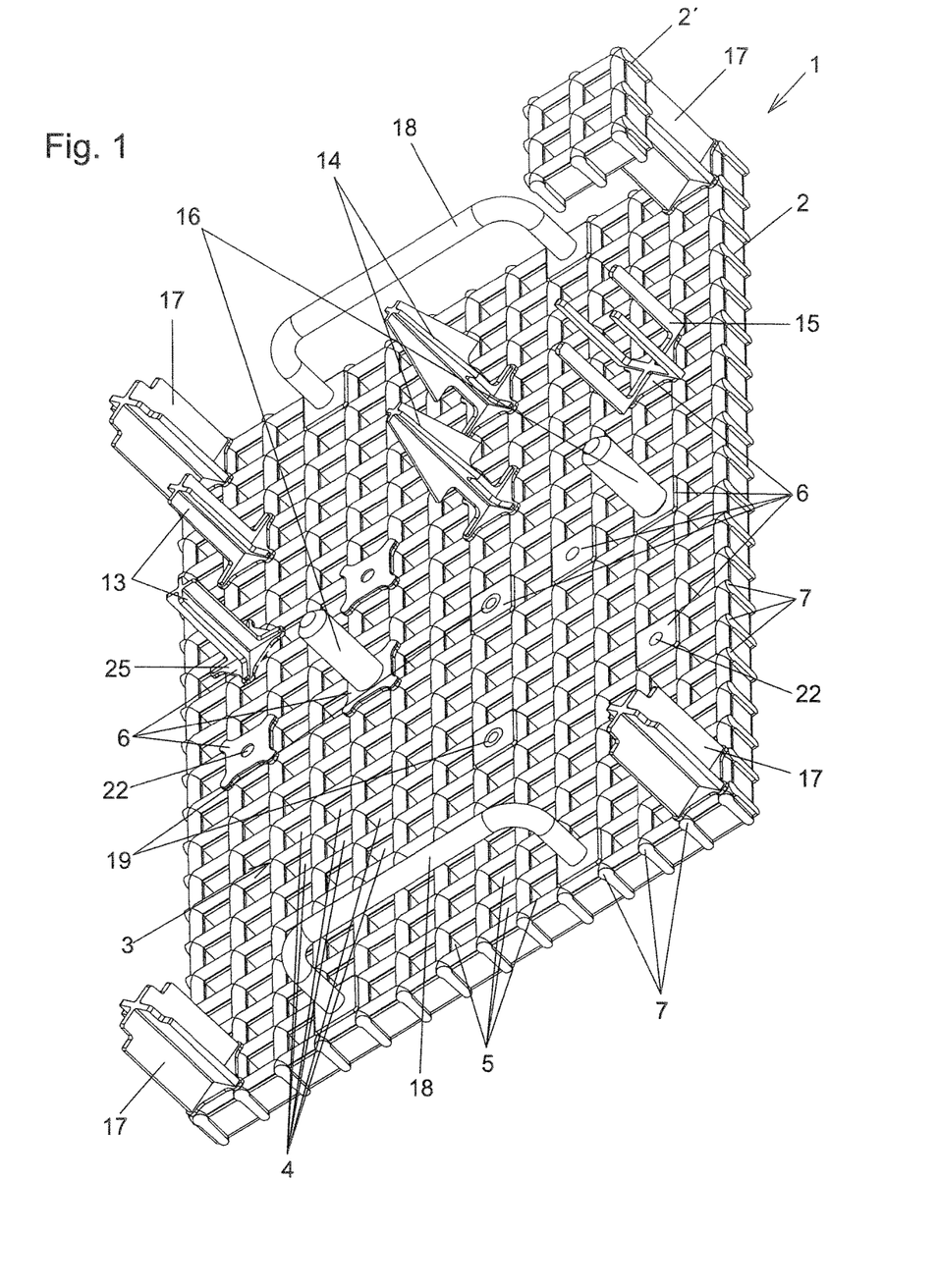
FIG. 1 shows a perspective view of an illustrative embodiment of a carrier arrangement according to the invention.
Figure 4:
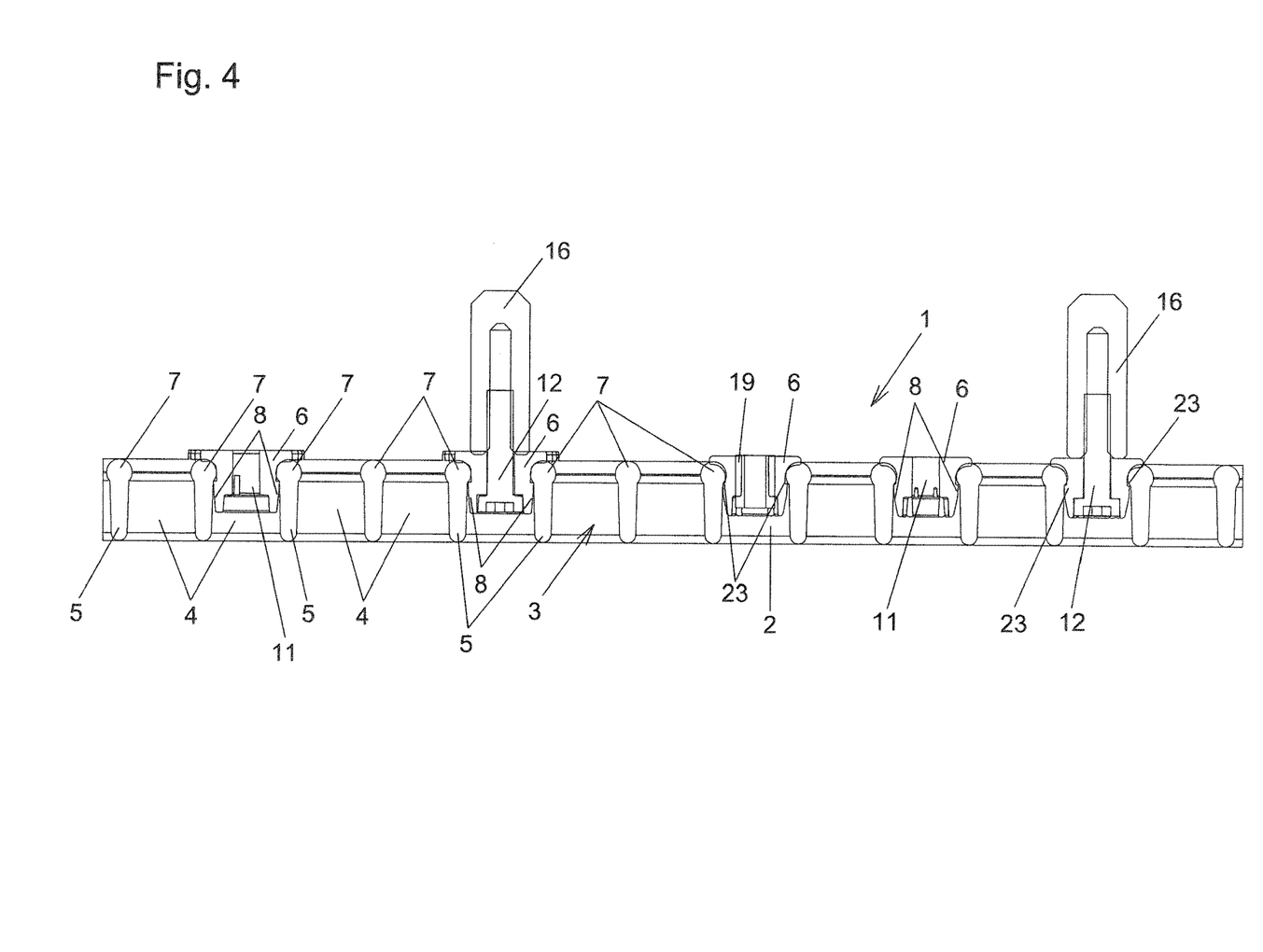
FIG. 4 shows a longitudinal section through a partial area of this illustrative embodiment.
Figure 5:
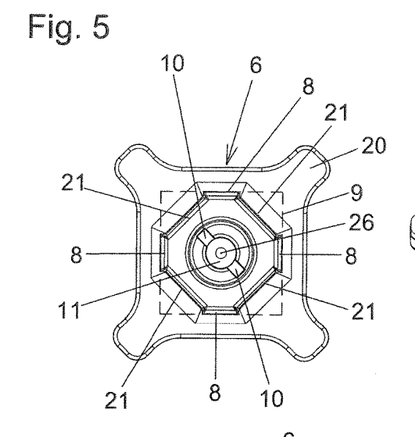
FIGS. 5 to 9 show views of a first illustrative embodiment of a first type of fastening base for this carrier arrangement.

The carrier plate 2 of the carrier arrangement 1 shown here in FIG. 1 has, in this illustrative embodiment, square openings 4 which are each surrounded by lattice rods 5 correspondingly arranged in a square. The openings 4 of this lattice structure 3 in this illustrative embodiment are designed as through-holes and all have the same size. This is preferably also chosen in other preferred embodiments of the carrier arrangement 1. The latter has the advantage that the fastening bases 6 are fastenable with a clamping action in all of the openings 4. According to the invention, each of the fastening bases 6 shown here is fastened with a clamping action in one of the openings 4, which here have a square shape. A wide variety of supporting structures or other structures or components can be fastened integrally or releasably on the fastening bases 6. For example, in this illustrative embodiment, the grips 18 are shown which are fastened with a clamping action on the carrier plate 2 by means of fastening bases 6 according to the invention. Furthermore, in this illustrative embodiment, the different fastening bases 6 also carry a wide variety of supporting structures, e.g. the cross-shaped uprights 13, the fir-tree-shaped uprights 14, the multi-fingered uprights 15, and also the rod-shaped uprights 16. The cross-shaped, fir-tree-shaped and multi-fingered uprights 13, 14, 15 are each integrally formed on the corresponding fastening base 6. As can be seen in FIG. 4, the rod-shaped uprights 16 are screwed onto the respective fastening base 6 by means of in each case one of the expansion screws 12. Some of the fastening bases 6 shown here carry a threaded bush 19 in their interior. Any other components can then be fastened on this threaded bush by screwing. In preferred embodiments, both the carrier plate 2 and the fastening bases 6 are expediently made from plastic. The alternatives to this have already been mentioned at the outset. However, the threaded bushes 19 are preferably made of metal. Instead of the threaded bushes 19, however, the fastening bases 6 can also have simple fastening holes 22, in which corresponding supporting structures or other structures can then be fastened in a suitable manner. In a departure from the illustrative embodiment shown here, wall-shaped structures can also be fastened with a clamping action in the carrier plate 2 via corresponding fastening bases 6, e.g. in order to form corresponding baskets.

In FIG. 1, stacking uprights 17 are provided at the four corners of the carrier plate 2 by means of corresponding fastening bases 16. These stacking uprights 17 serve to allow a further carrier plate 2' of a further carrier arrangement 1 to be stacked on them and thus on the carrier arrangement 1 shown. This is indicated in the upper right-hand corner of FIG. 1.

The beads 7 of the lattice rods 5, which beads 7 are in this case of at least partially circular cross section, can also be clearly seen in the perspective view according to FIG. 1. In the illustrative embodiments shown here, the beads 7 serve to fasten the fastening bases 6 in the respective opening 4.

Figure 2:
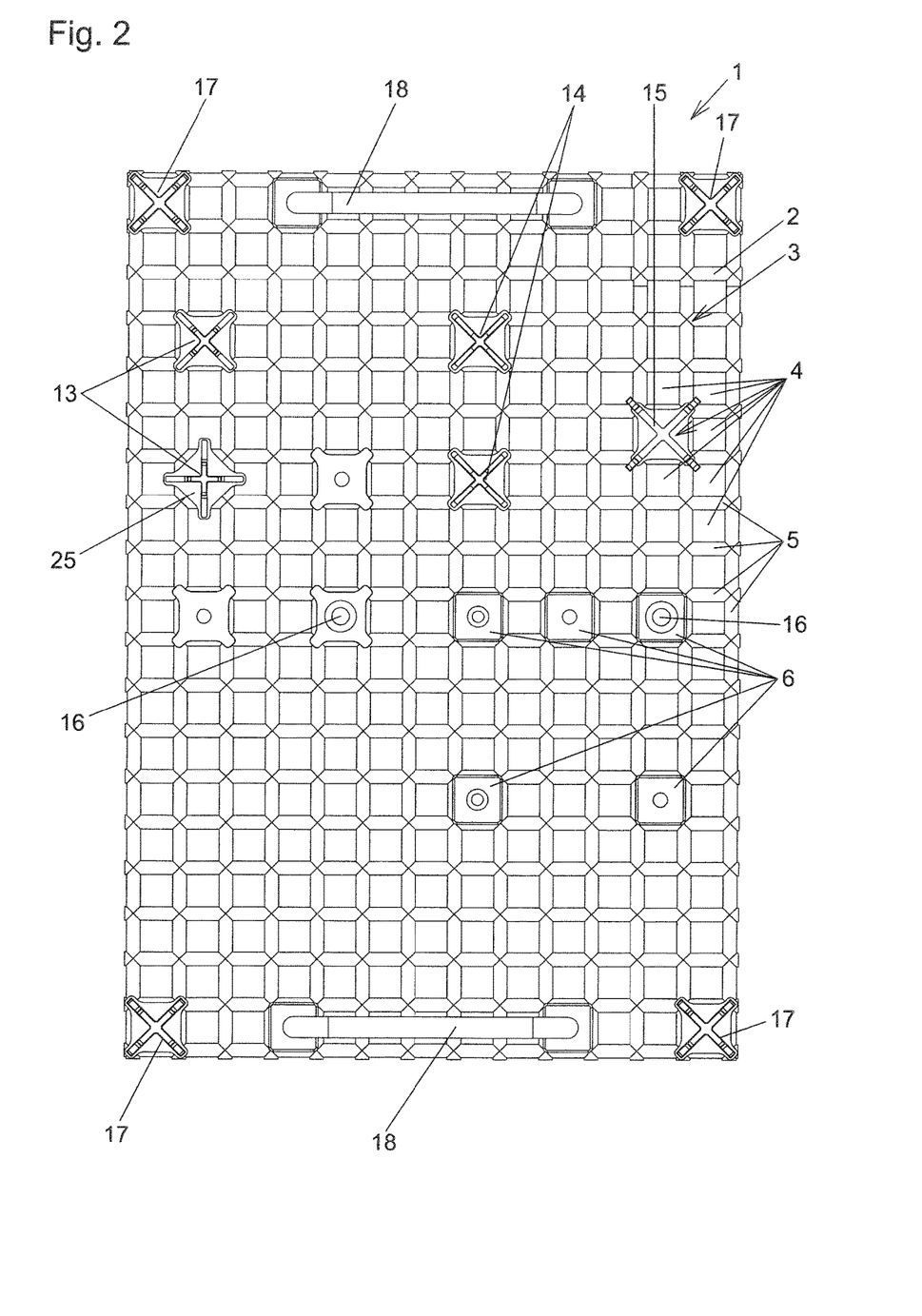
FIG. 2 shows a plan view of this illustrative embodiment.

FIG. 2 shows a plan view of the carrier arrangement 1 according to FIG. 1, but the stacked-on further carrier plate 2' indicated at the upper right-hand edge in FIG. 1 has been omitted. FIG. 2 shows particularly clearly that each of the fastening bases 6 is fastened with a clamping action in a respective one of the here square openings 4.

Figure 3:
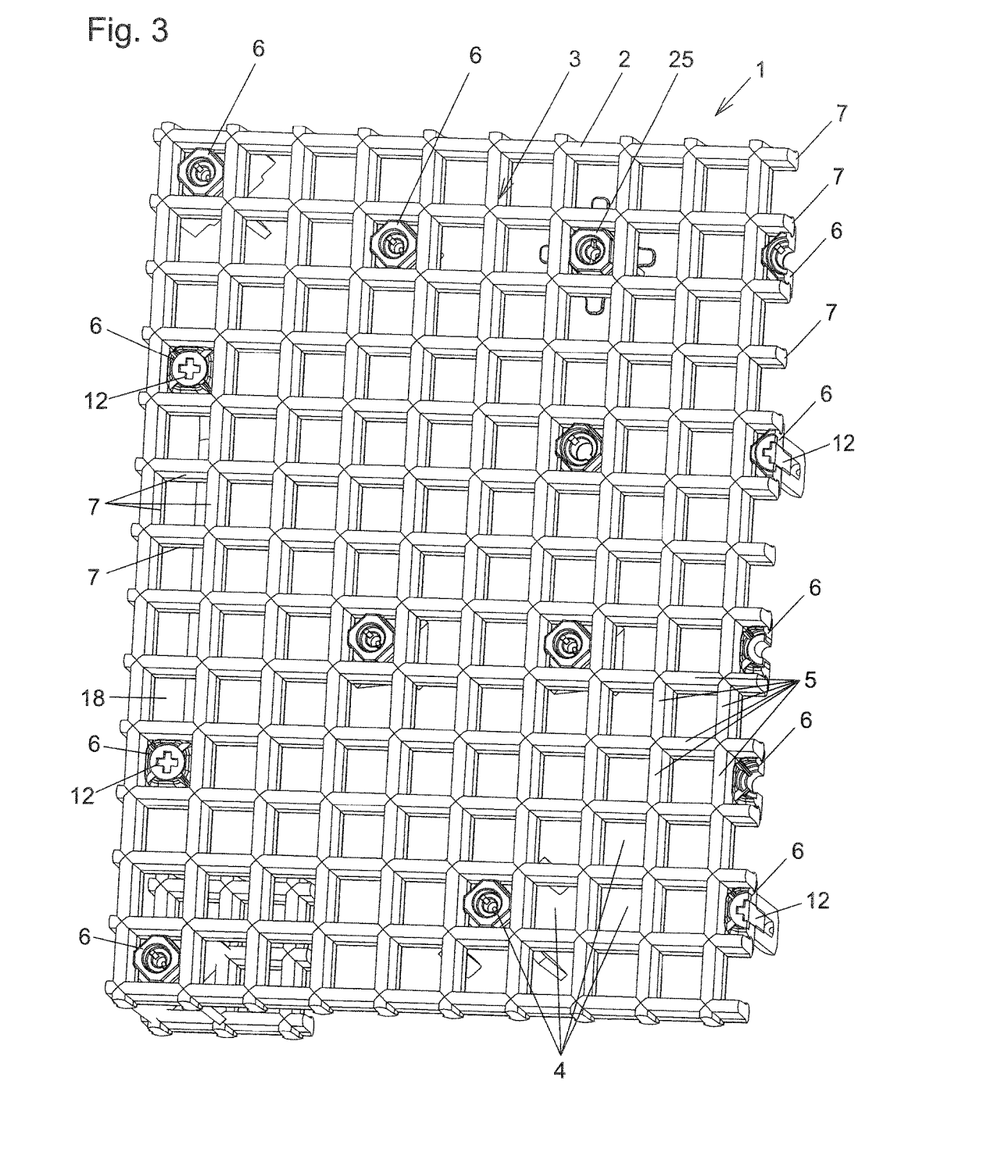
FIG. 3 shows a bottom view of a partial area of this illustrative embodiment.

FIG. 3 shows a bottom view of a partial area of the carrier arrangement 1 from FIG. 1.

In FIGS. 1 to 3, all but one of the fastening bases 6 are shown in the position in which they are fastened with a clamping action in the respective square opening 4. The sole exception to this is the fastening base designated by reference sign 25. As will be explained in further detail below, this fastening base 25 is already inserted into the opening 4 but has not yet been fastened in the latter with a clamping action.

The cross-sectional view according to FIG. 4 clearly shows, in the first instance, the configuration of the beads 7 on the lattice rods 5 on one of the surfaces of the carrier plate 2. It can also be clearly seen how, in the illustrative embodiments shown, the latching tongues 8 of the different fastening bases 6 engage with their undercuts 23 behind the beads 7, in order thereby to fasten the respective fastening base 6 according to the invention with a clamping action in a respective one of the openings 4. The latching tongues 8 are each accordingly pre-stressed elastically in the direction in which they engage behind the bead 7.

Between the latching tongues 8, all of the illustrative embodiments of fastening bases 6 shown here have recesses 11 into which an expansion pin, or here an expansion screw 12, can be introduced. The expansion screws 12, like the expansion pins not shown here, support the latching tongues 8 such that the latter can no longer be deflected from their clamped position, with the result that the respective fastening base 6 is fastened with a particularly firm clamping action in the respective opening 4. As is also shown here, the expansion screws 12 can at the same time be used to fasten corresponding supporting structures or other components on the fastening base 6. In FIG. 4, this is illustrated by the example of the rod-shaped upright 16 fastened on the respective fastening base 6 by means of the expansion screws 12.

FIGS. 5 to 9 show an illustrative embodiment of a first type of fastening base 6 which is fastenable with a clamping action on the lattice-shaped structure 3 by means of the fastening base 6 being inserted into the opening 4 and by means of the fastening base 6 then being rotated in the opening 4. For this purpose, the fastening base 6 is rotated about the rotation axis 26. As can be seen particularly clearly in the bottom view shown in FIG. 5, the fastening base 6 has four pairs of opposite latching tongues 8. The latching tongues 8 lying opposite each other in respective pairs are elastically pre-stressed in the abovementioned manner. The four latching tongues 8 extend at least in part along the faces of an imaginary square 9, which is likewise indicated in FIG. 5. Between two respectively adjacent latching tongues 8 there is an intermediate face 21, which is arranged at a shorter distance than the latching tongues 8 from the rotation axis 26. In preferred embodiments, like the one shown here, the latching tongues 8 and the intermediate faces 21 provide what is overall an octagonal structure, in this case also one that has axial symmetry and also point symmetry.

Located between the latching tongues 8 is the recess 11 into which an expansion pin or an expansion screw 12 can be screwed in order to support or fix the latching tongues 8 in their clamping position. Moreover, the fastening base 6 according to FIGS. 5 to 9 also has recesses 10 for the engagement of a rotary tool. In the illustrative embodiment shown here, the two recesses 10 form a slit for a screwdriver. The latter can be used to rotate the fastening base 6 about the rotation axis 26, so as to fasten the fastening base 6 with a clamping action in the opening 4 or also to release this clamping fastening again.

Figure 6:
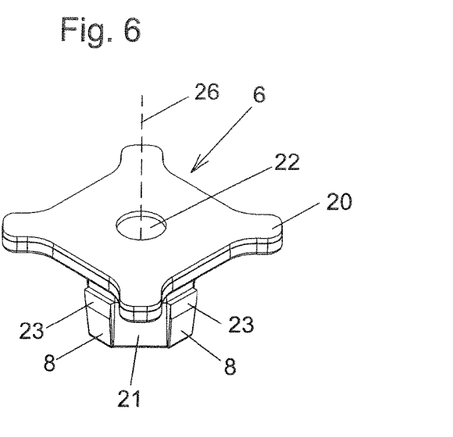
Figure 7:
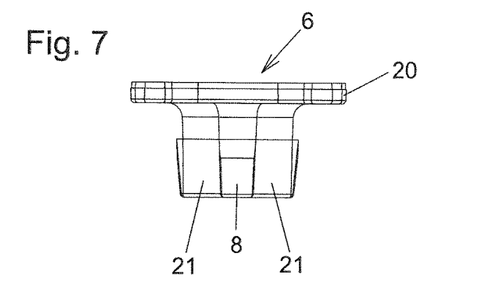
Figure 8:
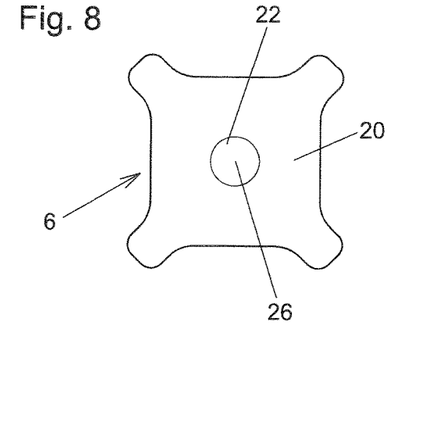
Figure 9:
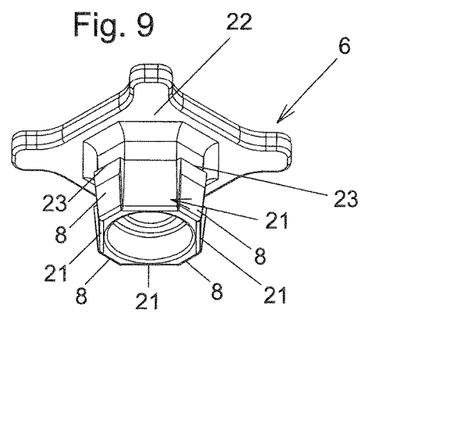

The respective undercut 23 on the latching tongues 8 can also be clearly seen in the perspective views in FIGS. 6 and 9. With this undercut 23, the latching tongues 8 engage behind the beads 7, as is shown in FIG. 4.

In the illustrative embodiments shown here, the fastening base 6 also has a plate 20. In the illustrative embodiments shown here, this plate 20 serves as a kind of abutment, such that the respective bead 7 can be clamped, preferably free of play, between the latching tongues 8 and the plate 20. A wide variety of supporting structures or other structures or the like can be fastened on the fastening hole 22.

As can also be clearly seen in FIG. 4, provision is made in preferred illustrative embodiments of the invention that, when the fastening base 6 is fastened in an opening 4, the lattice rods 5 protrude above the respective fastening base 6 on one side of the lattice-shaped structure 3. This has the effect that the fastening bases 6 on this side of the carrier plate 2 are concealed between the lattice rods 5 and, on this side of the carrier plate 2, do not protrude beyond same. The side in question is expediently the side of the carrier plate 2 arranged opposite the beads 7. This has the effect that the fastening bases 6, when fastened in an opening 4 of the carrier plate 2, do not protrude downward beyond the carrier plate 2. This makes it possible, for example, to slide the carrier plate 2 over an even support surface, without the fastening bases 6 being able to collide with this support surface.

Figure 10:
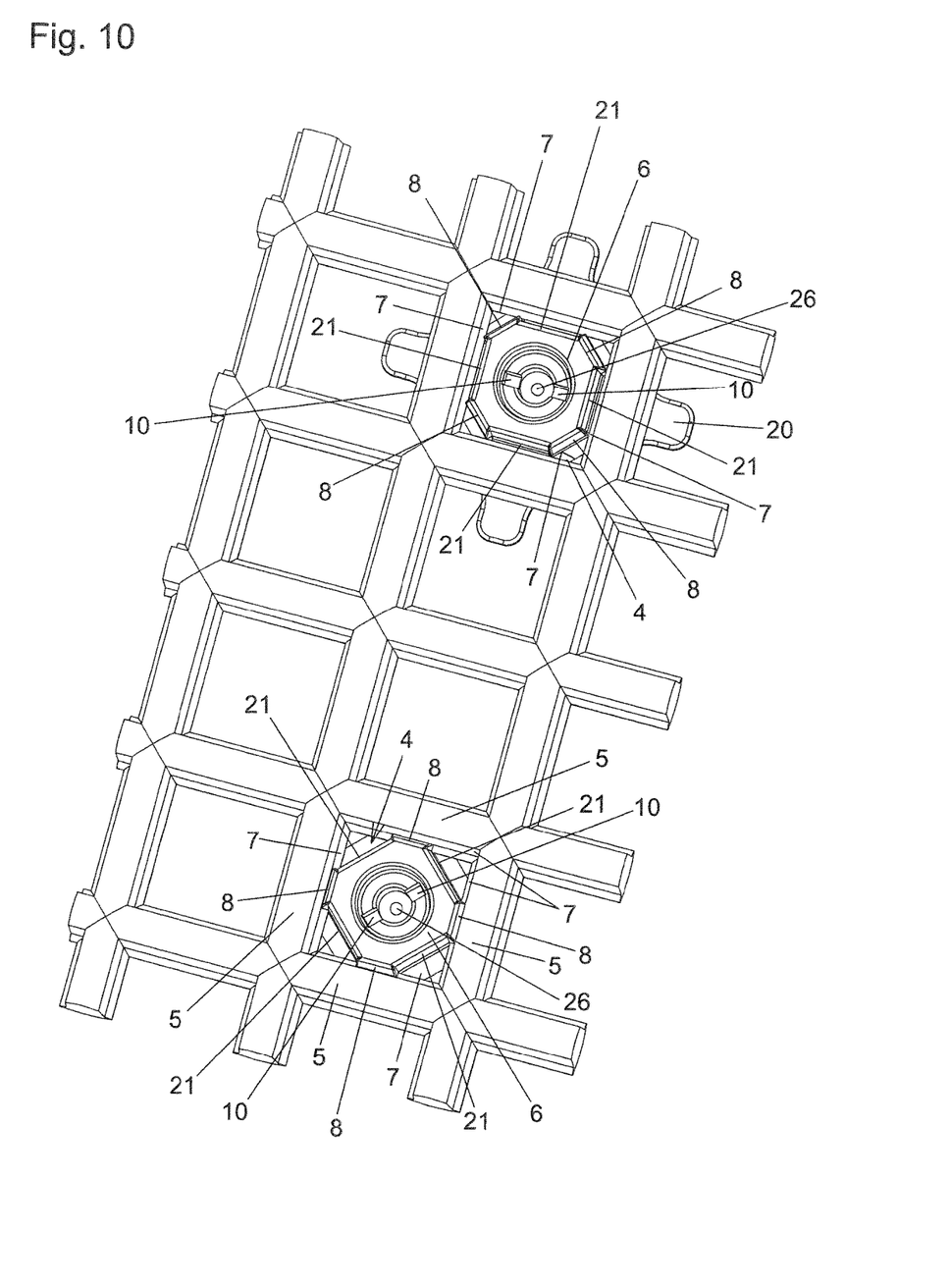
FIG. 10 shows a view depicting how the fastening base of the type shown in FIGS. 5 to 9 is fastened in the lattice-shaped structure.
Figure 11:
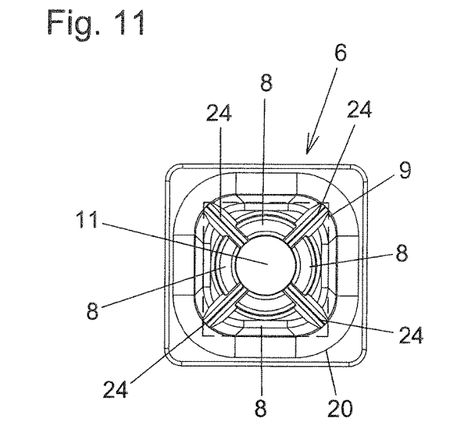
FIGS. 11 to 15 show a second type of fastening base according to the invention.
Figure 12:
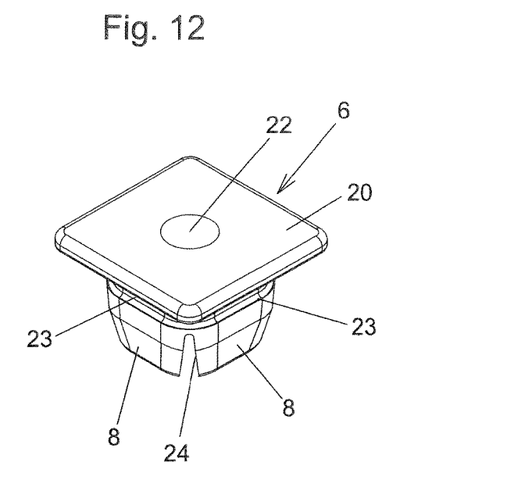
Figure 13:
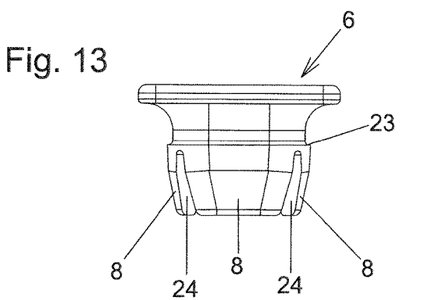
Figure 14:
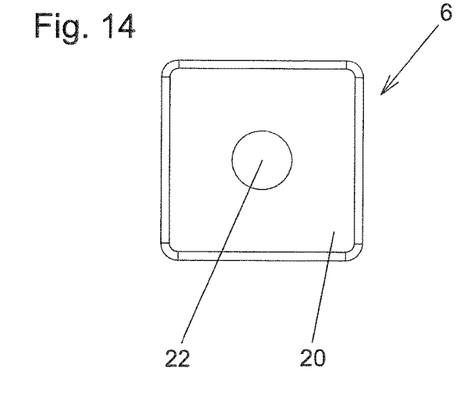
Figure 15:
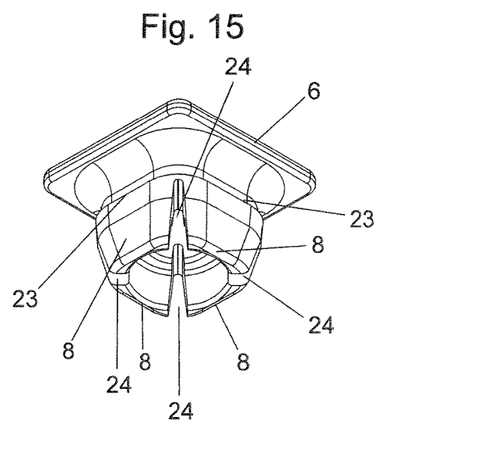

FIG. 10 serves to explain the way in which the fastening base according to FIGS. 5 to 9 is fastened in the opening 4 of the lattice-shaped structure 3 of the carrier plate 2. To fasten the fastening base 6 in an individual opening 4 of the lattice-shaped structure 3, the fastening base 6 is inserted linearly into the opening 4 in the position shown above in FIG. 1n this position, the intermediate faces 21 are oriented parallel to the lattice rods 5. Since the intermediate faces 21 lie closer to the rotation axis 26 than do the latching tongues 8, an insertion of the fastening base 6 into the opening 4 is easily possible in this position. Once the fastening base 6 with its latching tongues 8 is inserted into the opening 4 in the appropriate manner, the fastening base 6 is turned about the rotation axis 26, e.g. by insertion of a screwdriver into the recess 10, until the latching tongues 8 engage with a clamping action behind the beads 7, whereby the fastening base 6 is then fastened with a clamping action in the opening 4. The corresponding end position is shown at the bottom of FIG. 10.

In this end position, it is also possible, if deemed necessary, for the corresponding expansion screw 12 to be screwed into the recess 11, whereby the latching tongues 8 are then additionally supported at the rear in order to achieve a particularly firm and stable clamped connection between fastening base 6 and lattice-shaped structure 3.

If the fastening base 6 is to be returned from the position shown at the bottom of FIG. 10 to the position shown at the top of FIG. 10 in order to remove the fastening base 6 from the opening 4, it is possible for the fastening base 6 to be rotated onward in the same direction in which it was rotated to the clamped position. Alternatively, it is also possible for it to be rotated back in the corresponding opposite direction about the rotation axis 26. In the position shown in FIG. 10, the fastening base 6 can then be easily removed again from the opening 4.

FIGS. 11 to 15 show an example of an alternative type of fastening base 6. This type of fastening base 6 is intended for the purpose that the fastening base 6 is fastened with a clamping action on the lattice-shaped structure 3 exclusively by means of the fastening base 6 being pressed, preferably linearly, into the opening 4. Here too, the four latching tongues 8 are arranged extending along an imaginary square 9. These latching tongues 8 also provide a structure that has axial symmetry and also point symmetry. Located between the respective latching tongues 8 there are gaps 24 which facilitate the elastic deformation of the latching tongues 8 when the fastening base 6 is being pressed into or removed from the opening 4 in the lattice-shaped structure 3, particularly when the latching tongues 8 have to be pushed in between the beads 7 or removed. Here too, the latching tongues 8 each have an undercut 23 with which they engage behind the bead 7. In the clamped position of the fastening base 6 in the opening 4, the beads 7 of the lattice rods 5 are clamped in between the plate 20 and the respective undercut 23 of the latching tongue 8. In this illustrative embodiment too, a recess 11 is provided between the latching tongues 8, into which recess 11 and expansion screw 12 or a corresponding expansion pin can be introduced, if necessary, in order to support the latching tongues 8 at the rear and thus achieve a particularly stable, clamped fastening of the fastening base 6 in the opening 4. A recess 11 for a rotary tool is not provided here, since this type of fastening base 6 is not rotated during insertion into and removal from the opening 4.

Figures 16, 17, 18, 19, 20:
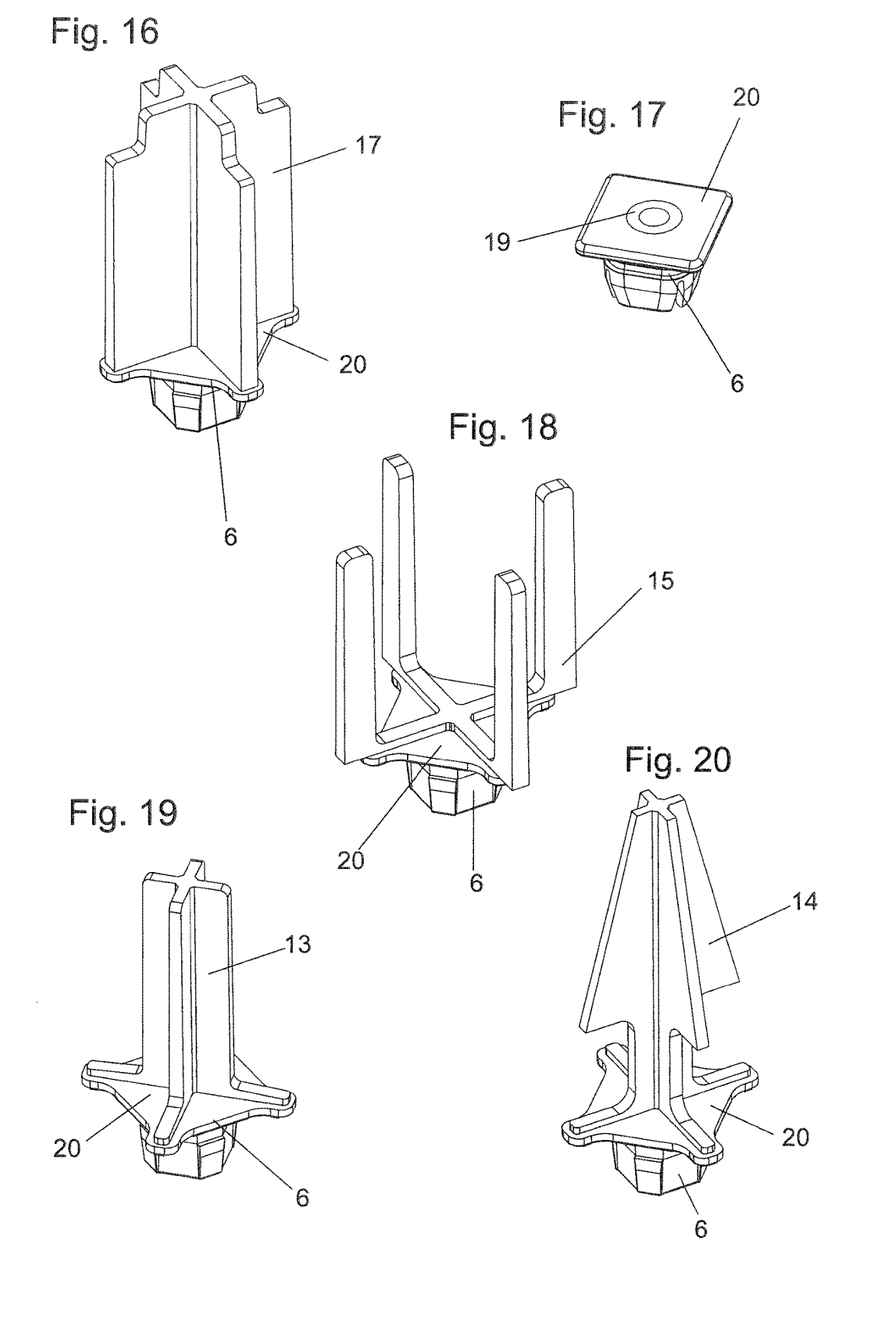
FIGS. 16 to 20 show different examples of supporting structures or other structures of the kind that can be used on fastening bases according to the invention.

FIGS. 16 to 20 again show fastening bases 6 according to the invention on which various examples of supporting structures are arranged. In FIGS. 16, 18, 19 and 20, the respective uprights 13, 14, 15 and 17 are each integrally formed in one piece. FIG. 17 shows an illustrative embodiment of a fastening base 6 in which a threaded bush 19, preferably made of metal, is provided, onto which any desired supporting structure or other kind of structure can be screwed.

KEY TO THE REFERENCE NUMBERS 1 carrier arrangement
2, 2' carrier plate
3 lattice-shaped structure
4 opening
5 lattice rod
6 fastening base
7 bead
8 latching tongue
9 imaginary square
10 recess
11 recess
12 expansion screw
13 cross-shaped uprights
14 fir-tree-shaped uprights
15 multi-fingered uprights
16 rod-shaped uprights
17 stacking uprights
18 grip
19 threaded bush
20 plate
21 intermediate face
22 fastening hole
23 undercut
24 gap
25 fastening base
26 rotation axis

The invention claimed is:

1. A carrier arrangement for at least one of storing, transporting, or cleaning items, the carrier arrangement comprising:
    at least one carrier plate with at least one lattice-shaped structure, the lattice-shaped structure formed by lattice rods which are arranged in a rectangular shape and surround rectangular openings,
    at least one fastening base which is fastened with a clamping action on the lattice-shaped structure, the fastening base is fastened with a clamping action in a single one of the rectangular openings,
    the lattice rods surrounding the openings each have at least one bead for fastening the fastening base with the clamping action in the opening,
    the fastening base has four latching tongues located opposite to one another to form pairs,
    the fastening base has a plate, the bead is clamped between undercuts of the latching tongues and the plate, and the undercuts of all the latching tongues of the fastening base are at a same distance from the plate, and
    all of the beads of the carrier plate form a common plane.

2. The carrier arrangement according to claim 1, wherein the at least one bead is configured on a face of the lattice rods that forms a surface of the carrier plate.

3. The carrier arrangement according to claim 1, wherein each of the latching tongues for fastening the fastening base in the opening engages behind the bead of one of the lattice rods surrounding the opening.

4. The carrier arrangement according to claim 1, wherein said latching tongues extend at least in part along sides of an imaginary rectangle.

5. The carrier arrangement according to claim 4, wherein an intermediate face of the fastening base is located between two respectively adjacent ones of the latching tongues, and the intermediate face is arranged at a shorter distance than the latching tongues from a rotation axis of the fastening base.

6. The carrier arrangement according to claim 1, wherein at least one of the carrier plate or the fastening base is made at least partially from plastic.

7. The carrier arrangement according to claim 1, wherein, when the fastening base is fastened in one of the openings, the lattice rods protrude above the fastening base on one side of the lattice-shaped structure.

8. The carrier arrangement according to claim 1, wherein the fastening base has at least one recess located between latching tongues on the fastening base for engagement of a rotary tool, and an expansion pin or an expansion screw is received in the recess of the fastening base.

9. The carrier arrangement according to claim 1, wherein the fastening base has a connector which is releasable without destruction and is used to fasten a structure on the fastening base.

10. The carrier arrangement according to claim 1, wherein the fastening base is fastened with the clamping action on the lattice-shaped structure exclusively by the fastening base being pressed into the opening.

11. The carrier arrangement according to claim 1, wherein the fastening base is fastened with the clamping action on the lattice-shaped structure by the fastening base being inserted into the opening and then being rotated in the opening.

12. The carrier arrangement of claim 1, wherein the lattice rods which are arranged in the rectangular shape are arranged in a square shape, and the rectangular openings are square openings.

13. The carrier arrangement of claim 1, wherein the latching tongues located opposite to one another in pairs are elastically pre-stressed in a direction away from each other.

14. The carrier arrangement of claim 1, wherein, in order to facilitate an elastic deformation of the latching tongues, a gap is arranged in each case between two respectively adjacent latching tongues.

15. A carrier arrangement for at least one of storing, transporting, or cleaning items, the carrier arrangement comprising:

at least one carrier plate with at least one lattice-shaped structure, the lattice-shaped structure formed by lattice rods which are arranged in a rectangular shape and surround rectangular openings, at least one fastening base which is fastened with a clamping action on the lattice-shaped structure, the fastening base is fastened with a clamping action in a single one of the rectangular openings, the lattice rods surrounding the openings each have at least one bead for fastening the fastening base with the clamping action in the opening, the fastening base has four latching tongues located opposite to one another to form pairs, the fastening base has a plate, the bead is clamped between undercuts of the latching tongues and the plate, and the undercuts of all the latching tongues of the fastening base are at a same distance from the plate, and the latching tongues located opposite to one another in pairs are elastically pre-stressed in a direction away from each other.

16. A carrier arrangement for at least one of storing, transporting, or cleaning items, the carrier arrangement comprising:

at least one carrier plate with at least one lattice-shaped structure, the lattice-shaped structure formed by lattice rods which are arranged in a rectangular shape and surround rectangular openings, at least one fastening base which is fastened with a clamping action on the lattice-shaped structure, the fastening base is fastened with a clamping action in a single one of the rectangular openings, the lattice rods surrounding the openings each have at least one bead for fastening the fastening base with the clamping action in the opening, the fastening base has four latching tongues located opposite to one another to form pairs, the fastening base has a plate, the bead is clamped between undercuts of the latching tongues and the plate, and the undercuts of all the latching tongues of the fastening base are at a same distance from the plate, and each of the latching tongues for fastening the fastening base in the opening engages behind the bead of one of the lattice rods surrounding the opening.

* * * * *